United States Patent [19]

Hirshorn et al.

[11] 4,414,979

[45] Nov. 15, 1983

[54] MONITORABLE BONE GROWTH STIMULATOR

[75] Inventors: Michael S. Hirshorn, Sydney; David K. Money, Pennant Hills; Stephen J. Swift, Hornsby; Robert J. Evans, Chatswood, all of Australia

[73] Assignee: Telectronics Pty. Ltd., Lane Cove, Australia

[21] Appl. No.: 237,089

[22] Filed: Feb. 23, 1981

[51] Int. Cl.$^3$ .............................................. D61N 1/20
[52] U.S. Cl. ................................................. 128/419 F
[58] Field of Search ...... 128/419 F, 419 PG, 419 PT, 128/419 R, 419 PS, 419 E, 903

[56] References Cited

U.S. PATENT DOCUMENTS

| | | | |
|---|---|---|---|
| 2,827,056 | 3/1958 | Degelman | 128/422 |
| 3,453,546 | 7/1969 | Fryer | 128/903 |
| 3,842,841 | 10/1974 | Brighton et al. | 128/419 F |
| 4,026,305 | 5/1977 | Brownlee et al. | 128/419 PG |
| 4,124,031 | 11/1978 | Mensink et al. | 128/419 PG |

Primary Examiner—William E. Kamm
Attorney, Agent, or Firm—Gottlieb, Rackman and Reisman

[57] ABSTRACT

There is disclosed an implantable bone growth stimulator whose direct-current output can be monitored. Rather than to interrogate the device, e.g., by using a control magnet as in the heart pacer art, the device continuously transmits pulses of electromagnetic energy at a rate proportional to the current being delivered. The continuous transmission expends no more than about five percent of the total power. Instead of using an electrode lead as an antenna for radiating the pulses, a separate coil inside the device is utilized so that the therapeutic current itself is in no way affected by the pulse transmission. Effective transmission is achieved despite the fact that the device is hermetically sealed in a titanium case. Also included is an electronic switch for drastically limiting power drawn from the battery until implantation takes place, in order to provide an extended shelf life.

23 Claims, 5 Drawing Figures

MONITORABLE BONE GROWTH STIMULATOR

This invention relates to monitorable implantable tissue stimulators, and more particularly to an implantable bone growth stimulator whose therapeutic current may be monitored.

In the copending application of Wickham et al, Ser. No. 059,443, filed July 20, 1979 and entitled "Bone Growth Stimulator", now U.S. Pat. No. 4,333,469 there is disclosed a bullet-shaped bone growth stimulator for promoting bone-bone fusion, i.e., bone growth, by electrical stimulation. The Wickham et al application, which is hereby incorporated by reference, describes the general background of bone growth stimulators. Such a device is simply a constant-current source. One or more cathode leads from the device are implanted in bone, in the area of a fracture. The case itself, typically made of titanium but preferably plated in at least a limited area with platinum, may serve as the anode, although a separate anode lead may be provided for insertion in soft tissue. The Wickham et al device is not hermetically sealed as is now standard practice in the heart pacer art; a heart pacer typically must withstand the hostile body environment for many years, while a bone growth stimulator has a useful life of only several months at best.

Bone growth stimulators have recently enjoyed increased use, and with that use there has arisen a desire for certain features which appear to be incompatible. Despite the fact that a bone growth stimulator is generally required to work for only a few months and will usually not fail even in the absence of hermetic sealing, many physicians are reluctant to implant any electronic prosthesis which is not hermetically sealed. Thus a preference has developed for hermetically sealing bone growth stimulators. At the same time, there has arisen a demand to allow the therapeutic current to be monitored, that is, to allow the physcan to determine at any time the magnitude of the current which is being delivered to the bone at the site of the implanted cathode(s). The apparent incompatibility of features is due to the fact that it is difficult to provide both hermetic sealing and monitor-ability in the same device.

In the case of a heart pacer, the fact that the device is hermetically sealed, i.e., encased in titanium, does not prevent monitoring of its operation. That is because any parameter to be monitored, e.g., battery potential, can be made to control the pacing rate, and the pacing rate can be ascertained by utilizing conventional ECG monitoring equipment. Upon application of an external magnet, the operating state of the pacer can be changed so that the pacing rate reflects the value of the parameter of interest. But in the case of a bone growth stimulator which delivers a constant DC current, there is no way in which a body surface potential can be measured to accurately indicate the magnitude of the current.

It might be thought that a cathode lead could be used as an antenna for radiating some kind of AC or pulse signal which might then be detected external of the body. The problem with this approach is that the signal current would necessarily flow through the bone, and could conceivably detract from the efficacy of the overall device and possibly even cause tissue damage.

It might similarly be thought that a prior art heart pacer technique could solve this problem. In the pacer art, the monitoring function is generally controlled by placing an external magnet over the patient's body in the vicinity of the pacer for operating an internal reed switch. Only when the reed switch is operated does the state of the pacer change to provide the desired monitoring capability. By utilizing a similar reed switch in a bone growth stimulator, it might be possible to control the application of an AC or pulse signal to a cathode lead not continuously, but rather only when an external magnet operates the switch. But this approach also suffers from several disadvantages. It is extremely difficult to actuate a reed switch through a plaster cast and body tissue, especially if the bone growth stimulator is implanted deeply in the body. The magnet would not only have to be costly and large in size, but it would probably have an adverse impact on the ferrite rod contained in any pick-up coil used in the external monitor and thus reduce its sensitivity to the transmitted signal. Furthermore, of all the components used in heart pacers, reed switches are probably the most unreliable and it would be best to avoid using one if at all possible.

In accordance with the principles of our invention, in the illustrative embodiment thereof, a continuous pulse signal is transmitted by the hermetically-sealed bone growth stimulator; thus an external magnet control and a reed switch are not required. Instead of using a cathode lead as an antenna, however, a separate internal coil is utilized. The pulses applied to the coil, at a rate proportional to the therapeutic current magnitude, are such that sufficient energy is transmitted through the 0.6 mm-thick titanium case for external monitoring. Thus the therapeutic current is in no way affected by the monitoring capability. The current pulses for actuating the internal coil are such that not only is sufficient energy transmitted, but the battery drain is so low that the device life is reduced by no more than five percent despite the fact that the monitoring signal is transmitted continuously. Furthermore, the circuit is designed such that prior to implantation current drain from the battery is minimal. Only upon implantation does the entire circuit begin to function, and it is only then that the monitoring pulses are generated. This feature greatly extends the shelf life of the device.

It should be understood that although the invention is described in the context of a bone growth stimulator which delivers a constant DC current to a fracture site, the principles of the invention are applicable to implantable tissue stimulators in general, even those which might deliver a pulse or alternating current to body tissue, e.g., a device which might be used for pain relief. In any such device, the use of our invention permits a condition or parameter to be monitored even though the device is encased in metal, without necessarily requiring use of an electrode lead as an antenna and while having a minimal effect on battery life.

Further objects, features and advantages of our invention will become apparent upon consideration of the following detailed description in conjunction with the drawing, in which.

Figure 1:
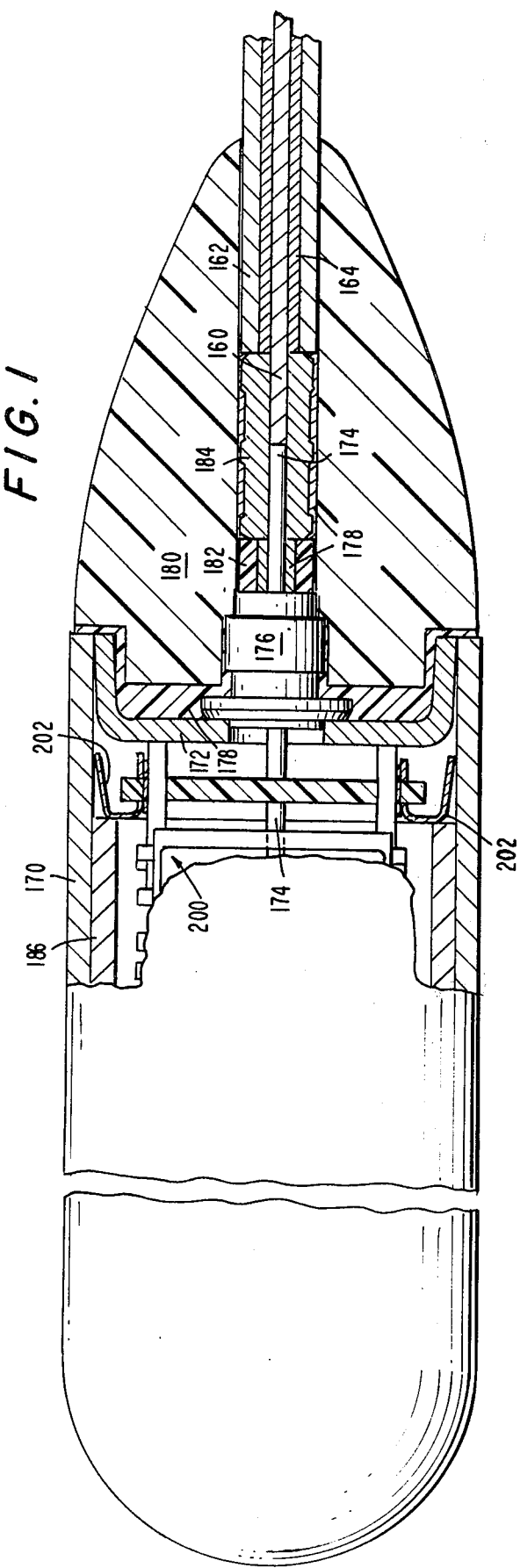
FIG. 1 depicts a preferred mechanical configuration for the illustrative embodiment of the invention.

The mechanical assembly depicted in FIG. 1 has the same type of bullet-shaped case as disclosed in the above identified Wickham et al application, but it is hermetically sealed by using the techniques which are now standard in the heart pacer art. The case 170 has a wall thickness of 0.6 mm, and is made of pure medical grade titanium. A polycarbonate insulating cup 186 is placed within the case 170, in order to insulate the electrical assembly 200 from the case. The electrical assembly itself is different from the type shown in the Wickham et al application in that it is constructed along the lines of heart pacers. Typically, two circuit boards are used with the electrical components placed between them, and with the integrated circuit chip being mounted on the sides between the boards. Pacer circuits often are provided with springs extending sideways for making contact with the case. The electrical circuit of our invention preferably includes two such springs 202, one on each side, for contacting the case 170 to the right of the rightmost edge of insulating cup 186. In this way, the anode connection of the circuit contacts the case directly, so that the case serves as the anode of the bone growth stimulator. The case 170 is 40 mm long, and has an external diameter of 10 mm.

Two battery cells are utilized to provide a potential source of 3.0 volts. At the start of life, there is approximately a 2.5-volt potential between the anode and the cathode. (Although the illustrative embodiment of the invention utilizes only a single cathode lead, as described in the Wickham et al application it is possible to use multiple cathode leads.) A constant current of 20 microamperes flows between the anode and cathode, even as the effective body resistance between the anode and cahode varies between very low values up to about 130K. The magnitude of the current falls as the battery voltage decreases with age, but since the batery voltage remains relatively constant over most of the life of the device, so does the current.

Titanium anodes can become polarized and can provide an effective resistance of up to 100K. This could lead to a substantial reduction in current after a relatively short use of the device and an "end-of-life" indication would be obtained too soon. For this reason, for about 10–15 mm at the rounded end of the case there is a 3–5 micron thick coating of platinum. The current actually flows from the platinum coating to the surrounding tissue, rather than from the remaining portion of the titanium case. The polarization potential developed at the platinum/tissue interface is much lower than that at a titanium/tissue interface, and this construction is highly preferred.

The case is hermetically sealed with a titanium top cap 172 which is welded along the edge which contacts the open end of the titanium case. A ceramic feed-through 176 is attached to the top cap in a brazing operation, with cathode conductor 174 extending from the circuit package through the feed-through. This type of construction is standard in the pacer art.

A Silastic top cover 180 is secured to the top cap 172 by Silastic "A" adhesive 178, the same materials as described in the Wickham et al application being suitable for use in the present invention. The cathode lead itself, three twisted wires identified by the numeral 160, is contained within Silastic tubing 162, with Silastic adhesive 164 filling the void around the lead. The lead itself extends into titanium sleeve 184, as does lead 174 from the circuit package. The sleeve is crimped to join the circuit lead to the electrode lead. Another short piece of Silastic tubing 182 separates the feed-through from the titanium sleeve, and to further fill the voids Silastic adhesive 178 surrounds both lead 174 within sleeve 182, and sleeve 184 within the Silastic top cover 180.

In general, the mechanical construction of the device is based on well-known techniques used in the pacer art. The important thing to note is that the circuit package is completely enclosed in a two-part titanium container, the case 170 and the top cap 172 being welded together. A reed switch can be incorporated in the circuit, in which case it could control the monitoring function only when actuated by a magnetic field as is standard practice with pacers, although, as mentioned above, it is more difficult to accomplish this in the case of a bone growth stimulator which is not only surrounded by a cast, but is also usually implanted more deeply in the body than is a heart pacer. But whether the monitoring is continuous or externally actuated, unless the cathode electrode lead is used as an antenna, the signal generated by the circuit must be capable of radiating through the case to an external monitor. Despite the apparent difficulty in transmitting a signal through the titanium case, it is possible to do so if the signal is made to have certain characteristics as will be described below.

Figure 2:
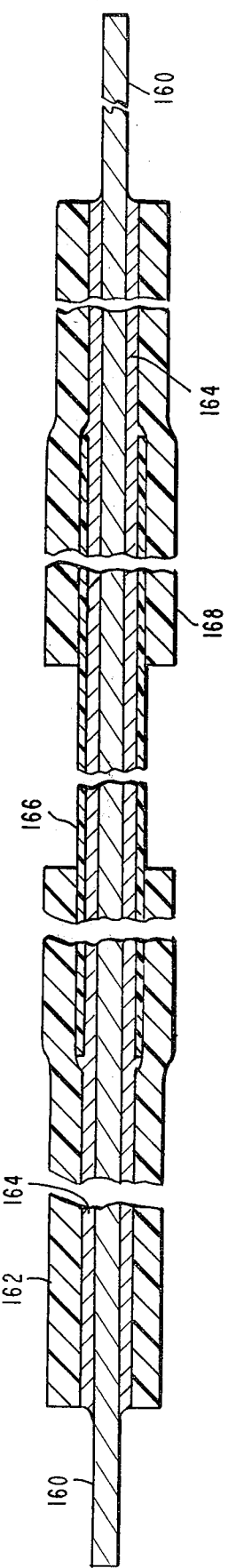
FIG. 2 depicts a preferred cathode electrode lead.

FIG. 2 depicts the construction of the cathode electrode lead itself, the construction being similar to that shown in the Wickham et al application. As previously described with reference to FIG. 1 and as shown on the left side of FIG. 2, the lead 160 is encased in Silastic tubing 162, with Silastic adhesive 164 filling the void between them. Although the Silastic tubing does not extend all along the lead, polyethylene tubing 166 does, with the left end of the polyethylene tubing being contained within the right end of the Silastic tubing. Similarly, on the other side of the lead another section of Silastic tubing 168 is employed, with Silastic adhesive 164 once again securing the Silastic tubing to the lead. The right end of the lead 160 may be coiled and implanted in the bone, as described in the Wickham et al application. Alternatively, as described in Dickson application Ser. No. 237,090, entitled "Bone Growth Stimulator Connector", filed on even date therewith and hereby incorporated by reference, a two-part connector may be used for coupling the lead 160 to a separate electrode which is actually inserted in the bone, thereby permitting simple disconnection of the stimulator from the electrode during explant, and also allowing the use of any of several different pre-formed electrodes with the same device. Lead 160 is made of titanium but, as described in the Dickson application, if a connector is used lead 160 may be of stainless steel for increased strength and only the implanted electrode, on the other side of the connector, should be made of titanium. The construction of the cathode lead has been shown and described only for the sake of completeness, it being understood that no claim for invention is made therein.

Although the cathode lead is made of titanium, it could be made of other materials. One such material is silver. By reversing the polarity of the output current, the silver electrode in the bone would function as an anode and silver ions would migrate from the anode to the surrounding tissue. This might have a therapeutic effect in the event of infection since it has been established that silver ions are useful in the treatment of infections. The current polarity reversal could be accomplished by using standard pacer techniques, e.g., by appropriately pulsing a reed switch in the device following which the polarity reversal might occur periodically for short intervals or until the device is reprogrammed. The principles of our invention are equally applicable to this kind of operation. In fact, in such a case it might be even more compelling to provide a monitoring function. For example, the signal radiated by the device might indicate not only battery voltage, but perhaps current polarity as well, the latter being useful in the event there is some doubt as to how the device has been programmed. Once again, what is required is a circuit which can radiate a signal, preferably directly through the case rather than along the electrode lead which would then function as an antenna.

Figure 3:
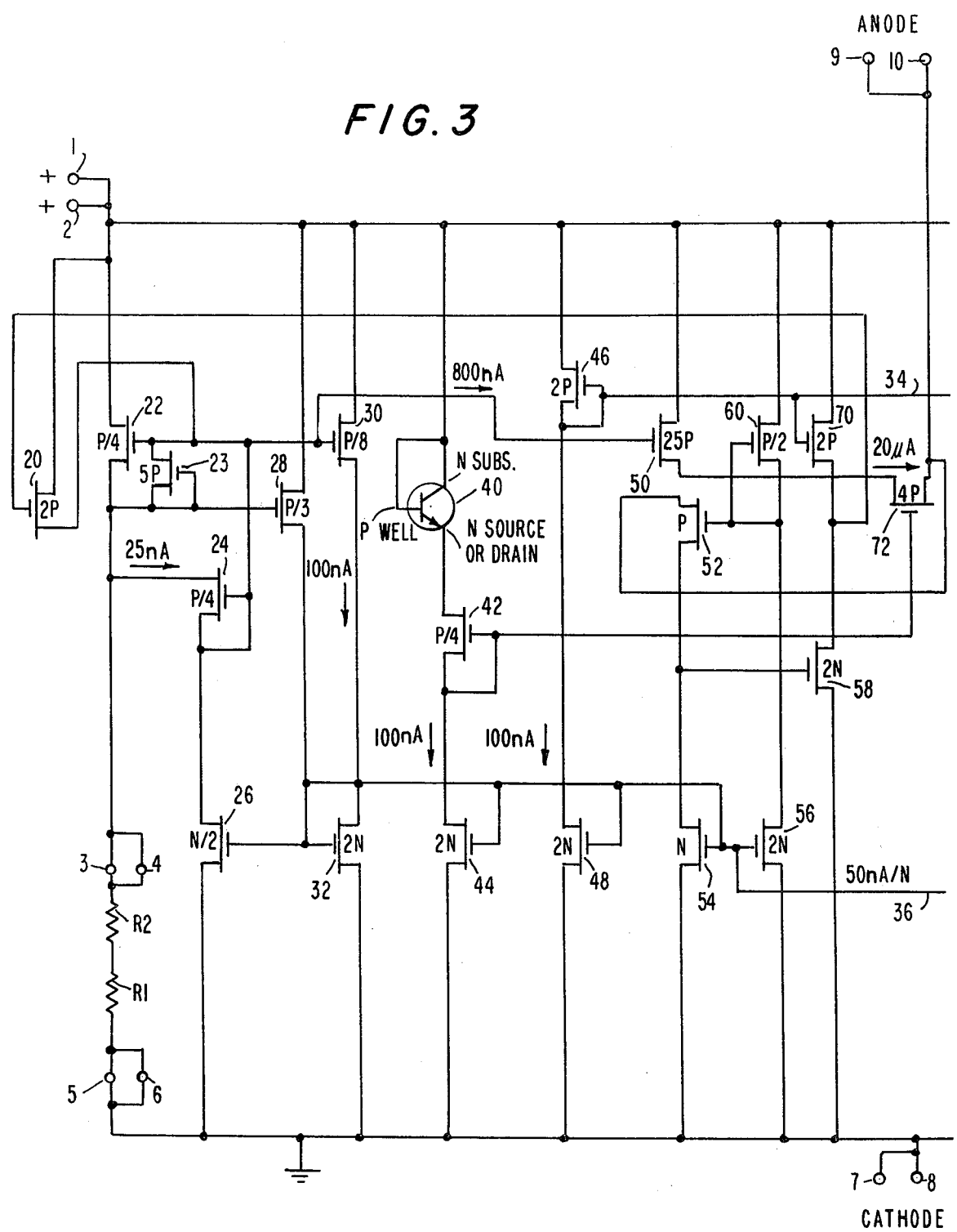
FIGS. 3 and 4 depict the electrical schematic of the illustrative embodiment of the invention.
Figure 4:
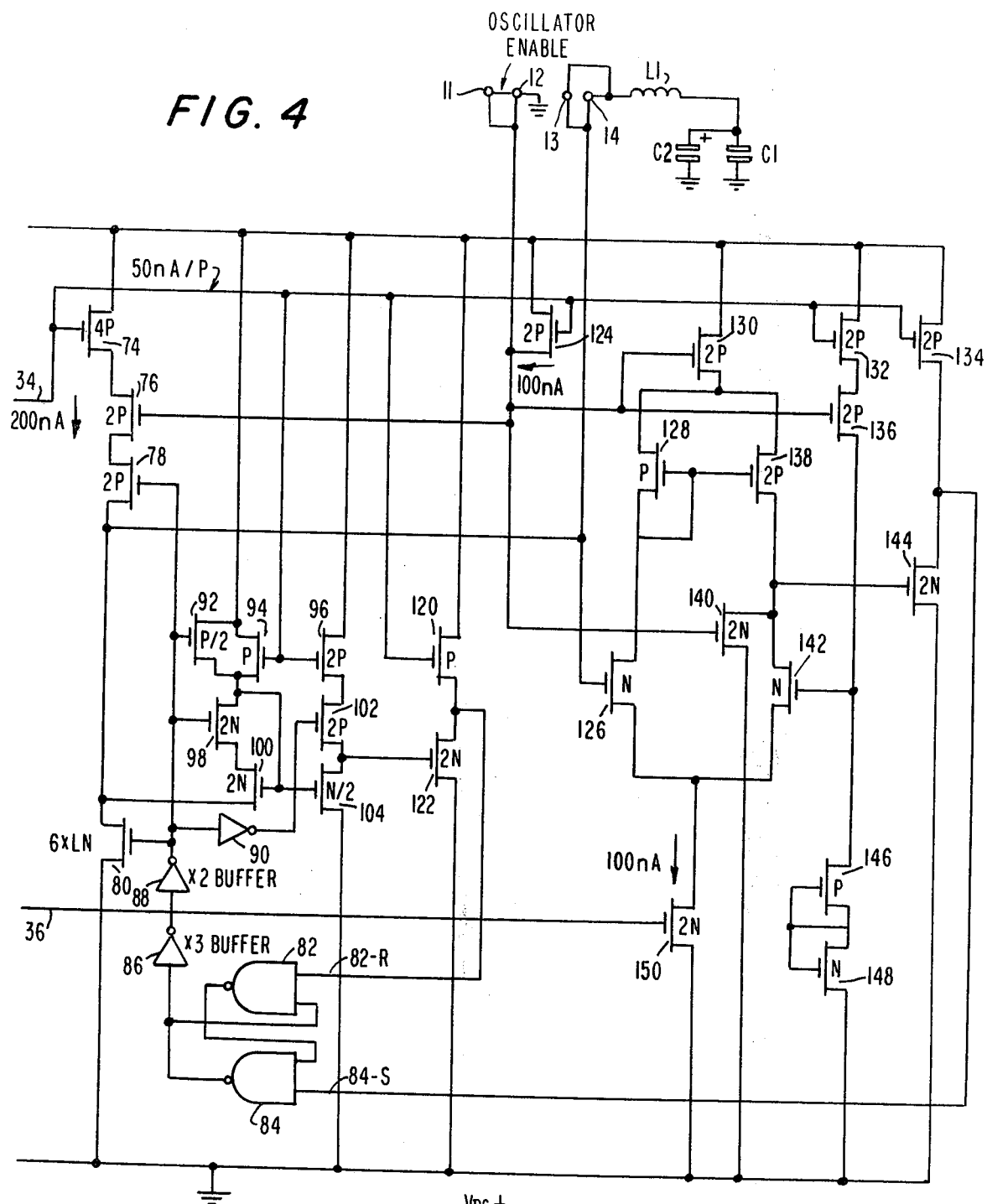

The circuit of FIGS. 3 and 4 includes two high-stability resistors R1, R2 for setting the constant current delivered by the device, two low-leakage capacitors C1, C2 for setting the monitoring pulse frequency, and a coil L1 for transcutaneous transmission of electromagnetic energy. The rest of the circuit consists of CMOS P-channel and N-channel enhancement mode FET's, preferably implemented on a semi-custom or full custom chip. The circuit performs the two functions of current delivery and monitor signal generation. The standard pacer technique of utilizing pairs of chip package pins for connection to peripheral components is utilized, the double pin connection in each case providing greater reliability. As shown at the top left of the drawing, pins 1,2 are used for connection to the positive battery terminal. As shown at the bottom left of the drawing, pins 5,6 are used for connecting the negative terminal of the battery to the chip. Resistors R1, R2 are connected between pins 3,4 and pins 5,6. Pins 9,10 are used for connecting the chip to the anode, in this case the titanium case, by the use of a pair of wire springs 202 as described above. The ground for the circuit is at pins 7,8, to which pins the cathode lead is connected.

The L1/C1/C2 combination, shown at the top right side of FIG. 4, is connected to pins 13,14. Finally, pins 11,12 are used to enable the monitoring circuit. The circuit is enabled whenever pins 11,12 are grounded, and in the illustrative embodiment of the invention they are wired to this state. Should the monitoring function not be required, the circuit can be held disabled simply by allowing the two pins to float. If external magnet actuation is desired, a normally-open reed switch should be connected between pins 11,12 and ground.

Each of the transistors in the drawing is identified as being a P-channel or N-channel device by use of the respective symbols P and N. Symbols such as 2P or N/2 refer to the width/length ratio of a particular device, i.e., its "on" impedance. A 2P device, for example, the a width/length ratio which is twice as great as that of a P device so that is conducts twice as much current for the same drain-source and gate-source potentials. (Alternatively, it may constitute two P devices connected in parallel.) Similarly, an N/2 device conducts only half the current of an N device. (It has half the "standard" width/length ratio, or else it comprises two standard devices connected in series, as is known in the art.) This nomenclature is standard in the art. Inverters or buffers 86,88 have associated with them the symbols ×3 and ×2. This simply refers to the fact that each of these inverters is in reality three or two inverters connected in parallel, each inverter being a two-transistor device as is known in the art. The symbol "6× LN" refers to device 80. A typical semi-custom array has transistors of several different sizes. A "large" transistor in the illustrative embodiment of the invention conducts fifty times as much current as a small one. Transistor 80 is in reality six of these large transistors connected in parallel. Each of the two NAND gates 82,84 comprises a pair of N-channel and a pair of P-channel transistors, as is known in the art.

Before proceeding with a description of the circuit, it will be useful at this point to describe transistor 40. Any CMOS chip can be provided with metalization which allows an effective bipolar transistor to be formed; bipolar devices are inherent in the chip itself. An N-channel device is made by first forming a P-well in the N-type substrate, with two N-type regions being formed in the P-well to serve as the source and drain. Either one of these N-type regions, together with the P-well and the N-type substrate constitute an NPN bipolar device. The N-type substrate of the overall semi-custom chip is connected to the positive supply terminal. By also connecting the P-well of a particular device to the positive supply and by using the source or drain of the device as the emitter, a bipolar transistor is formed which operates as a PN junction diode. As will be described below, diode 40 is used as a current limiter, and its emitter is 0.6 volt below the potential of the positive supply line since a PN junction drop is 0.6 volt.

A P-channel device requires its source voltage to be positive with respect to its drain voltage. It is for this reason that the P-channel devices are generally at the top of the circuit, with their sources extended to the positive supply line. An N-channel device requires a source voltage which is negative with respect to its drain voltage. It is for this reason that the N-channel devices are generally at the bottom of the drawing, with their sources connected to the negative (ground) supply line. A P-channel device requires its substrate to be connected to a positive potential while the N-channel device requires its substrate (the P-well) to be connected to a negative potential. This can be accomplished simply by connecting the substrate of the P type devices to the most positive voltage, and the P-wells to the most negative. Although the substrate connections are not shown in the drawing, it is to be understood that the substrate of each device is connected as detailed above.

A brief summary of MOSFET characteristics is also necessary in order to fully understand the operation of the circuit to be described below. When an MOS device is operated in its non-saturated region, i.e., when $V_{DS} \leq \Delta$, Then the drain current $I_{DS} = K(2\Delta V_{DS} - V_{DS}^2)$ where $\Delta = V_{GS} - V_T$ and $V_T$ is the threshold voltage. The parameter $\Delta$ is the effective drive for the device. It is in the non-saturated region that the drain-source current varies appreciably not only with the gate-source voltage ($V_{GS}$) but also with the drain-source voltage ($V_{DS}$). In the saturated region, where $V_{DS} \geq \Delta$, the drain-source current is characterized by the relationship $I_{DS} = K\Delta^2$. In this case, the drain-source voltage has little impact on the current, and the characteristic curves are essentialy flat with the current depending only on the gate-source voltage. The parameter K is a device constant, in units of $\mu A/V^2$. It is both process and area dependent, but for any chip the value of K for any device varies only with its area since the same process parameters apply to all devices. That is why the relative conductions in different devices, represented by symbols such as 2P and P/2, can be controlled by varying the areas.

The overall circuit includes a current reference source, shown on the left side of FIG. 3, for setting up a current reference which in turn controls current values throughout the circuit. In the illustrative embodiment of the invention, it is highly desirable for the current reference to be a function of only resistors R1, R2 and the battery potential. One reason for this is that the therapeutic current which flows through the cathode lead is a fixed multiple of the current reference; thus if the current reference is proportional to the battery potential, the monitoring signal, which is dependent on the current, will actually provide an indication of the battery potential since the resistance is fixed. A further advantage of the particular current reference circuit employed is that it requires only relatively few values of resistances to be stocked, even though chip characteristics may vary widely from batch to batch. As will be explained below, in all cases the desired current reference can be obtained by selecting from only a few stock values. The current reference circuit comprises transistors 30, 32 and the various devices to the left of them on FIG. 3.

The purpose of the current reference circuit is to develop a 100-nA current through transistors 30,32. By utilizing current-mirroring techniques, this current reference determines quiescent currents throughout the remainder of the circuit. It will be noted, for example, that the gates of all of transistors 32, 44, 48 and 56 are tied together, and the sources of all five of these devices are connected to the negative rail. Consequently, all five devices have the same gate-source potential. If any of the devices is operated in its saturated region, the drain-source current is essentially independent of the drain-source voltage, and depends only upon the gate-source bias. Consequently, the currents through the several devices depend only upon the relative device areas. Since 100 nA flows through transistor 32, and this transistor as well as transistors 44, 48 and 56 are 2N devices, 100 nA also flows through transistors 44, 48 and 56. (Transistor 54 conducts only 50 nA when it is on; as will be described below, it conducts only when transistors 44, 48 and 56 are on.)

Transistor 30 is a P/8 device, as indicated on the drawing, and it has 100 nA flowing through it. This means that a device with a width-length ratio eight times greater, i.e., a P device, whose gate-source voltage is the same, will have 800 nA flowing through it. That is the meaning of the 800 nA/P symbol on the lead from the gate of transistor 30. This lead is connected to the gate of transistor 50, whose source, as the source of transistor 30, is connected to the positive rail. Because transistor 50 is a 25P device, it has (25)(800) nA, or 20 μA flowing through it, as indicated in the drawing. Since only 50 nA flows through transistor 52, its current being controlled by current-mirror transistor 54, essentially all of the drain current of transistor 50 flows into the source of transistor 72 for delivery to the anode connected to pins 9,10. The current reference of 100 nA through transistor 30 thus directly controls the current delivered to the site to be stimulated. As the reference current decreases with decreasing battery potential, as will be described below, the stimulating current decreases in magnitude. Because the current reference is proportional (although not precisely) to the battery potential, the stimulating current is similarly proportional to battery potential. As will become apparent below, because the frequency of the signal transmitted from the device to an external monitor is also directly related to the current reference, the frequency of the transmitted signal provides an indication not only of the therapeutic current magnitude, but also of the battery potential.

The current reference circuit can be best understood by assuming that a current of 100 nA flows through transistors 30 and 32, as described above. Because the gate-source voltages of transistors 26 and 32 are the same, and one device has a width/length ratio four times as large as the other, only 25 nA flows through transistor 26. This current must be derived from the drain of transistor 24, and thus the drawing shows 25 nA flowing into the source of this device. Since the gate-source voltages of transistors 22 and 30 are the same, and the width/length ratios differ by a factor of two, 200 nA flows through transistor 22. This assumes that both transistors operate in the saturated region ($V_{GS} \geq \Delta$), since it is only in this region that the drain-source voltage has little effect on the current.

The operation of the current reference circuit is dependent upon the voltage drop between the source of transistor 30 and the source of transistor 24. Since the gates of the two devices are connected together, the voltage difference across the two sources is equal to the difference of the two gate-source voltages; in going from the source of transistor 30 to the source of transistor 24, there is a source-gate drop, followed by a gate-source drop. Since each $V_{GS}$ drop is equal to a $\Delta$ value plus $V_T$, when the two $V_{GS}$ drops are subtracted from each other to derive the total potential between the source of transistor 30 and the source of transistor 24, the $V_T$ terms cancel out and the total drop is equal to the difference between the two $\Delta$ values. The drop from the source of transistor 30 to the source of transistor 24 is thus very small since it is equal to the difference of the two $\Delta$ values. Because the source of transistor 30 is connected to the positive rail, there is a very small source-drain drop across transistor 22, i.e., the source of transistor 24 is very nearly equal to the battery potential. It is this voltage which appears directly across resistors R1 and R2, and since the potential across the resistors is for all intents and purposes equal to the battery potential, the current through transistor 22 is determined by Ohm's law, that is, it is equal to the battery potential divided by the total impedance. Resistors R1 and R2 are adjusted to provide a current of about 200 nA through transistor 22. This is the current which, as described above, is mirrored in transistor 30 to provide the current reference of 100 nA which was assumed in the first place.

The importance of the back-to-back gate-source voltages of transistors 30 and 24 is that the resulting drop across transistor 22 is not only very small, but it is also totally independent of $V_T$ and K. The reason why it is important for the current reference to be independent of process parameters will be described shortly, but first the importance of a low potential drop across transistor 22 should be appreciated. It is because this drop is so low that almost the full battery potential is impressed across resistors R1, R2, and it is in this manner that the current reference is made dependent only upon the battery potential and the magnitude of the impedance.

It should be noted that because the source-drain voltage of transistor 22 is very small, in the order of 100 millivolts, transistor 22 is not saturated. Thus the original assumption that transistor 30 mirrors the current through transistor 22 in a ratio of 1:2 is not entirely correct; current-mirror operation takes place only when two devices both operate in their saturated regions. Transistor 22 actually supplies slightly less current than the originally assumed 200 nA. But the current relationships are nevertheless approximately linear and that is the important thing. During manufacture, resistors R1, R2 are adjusted so that the anode current is 20 uA when a simulated load is connected between the anode and cathode of the bone growth stimulator. Thereafter, when the device is implanted, the therapeutic current varies with the battery potential. The monitoring signal provides an accurate representation of the therapeutic current magnitude, and a fairly good indication of the battery potential.

The importance of making the drop across transistor 22 independent of process technology is that $V_T$ can vary by as much as 25% from wafer to wafer. Suppose the drop across transistor 22 were dependent solely upon the gate-source voltage of only a single transistor 24, rather than transistor 30 as well. Since $V_T$ can vary from 0.4 volt to about 1 volt from wafer to wafer, resistors R1, R2 would have to vary over a wide range to provide the desired current reference. It would be necessary to stock up to 30 values of resistance. Although the resistors themselves are relatively inexpensive, if 100,000 units are made per year, it is apparent that the total cost of resistor stock would be very high.

But with the back-to-back connection of transistors 30 and 24, the drop across resistors R1, R2 is process independent, and varies only with $\Delta$ values and device area ratios. It is now possible to set the current through transistor 22 by stocking many fewer resistors. In the production of the illustrative embodiment of the invention, Cermet resistor R1 is selected from only four high-stability values of 15M, 16M, 16.4M and 18M, all of which are 1% precision components and have a 50 ppm temperature coefficient. These are the costly resistors and only four different values must be maintained in inventory. Carbon resistor R2 has a value in the 0–2M range, but there is no problem in stocking many different values since each of these resistors costs only about one cent; the resistors have a precision of only about 5% and a 200 ppm temperature coefficient. The advantage of the particular current reference circuit employed in that the total resistance range required for any device is only about 15–20M, whereas were the circuit dependent upon the manufacturing process a range twice as large would be necessary.

Another advantage of the current reference circuit employed is that as the battery voltage does start to fall, the various devices in the circuit do not become unpredictable in their operations until the potential drops very low. In fact, the circuit operation is predictable until the battery potential drops down to approximately the sum of the threshold voltages for a P-channel and N-channel device connected in series.

The circuit has been described thus far without reference to transistor 28. This transistor is a starting device. If transistor 22 is initially off even after the battery potential is applied, there is no current flow through any of the transistors in the circuit. Transistor 28 is provided to insure that transistor 22 turns on. In the absence of current through resistors R1, R2, the gate of transistor 28 is at ground potential since it is at the potential of the negative rail. Since the source of the device is connected to the positive rail, transistor 28 conducts and applies a positive potential to the gates of transistors 26 and 32. Both of these devices thus turn on, and the drain of transistor 26 goes low. Since the drain of transistor 26 is connected to the gate of each of transistors 22 and 30, both of these devices turn on. Once current starts to flow in this manner, transistor 28 actually turns off. When transistor 22 is on, its drain voltage is equal to the supply potential, less the source-drain drop across the device which is only about 100 millivolts as described above. Thus the gate-source voltage of transistor 28 is only 100 millivolts, and this is too low to maintain conduction. Transistor 28 is provided only to insure that current flows in the remainder of the circuit; it is a starting device, which is not needed once it first does its job.

The purpose of transistor 40 is to limit the current delivered to anode pins 9,10 in the event transistor 50 shorts. The 20 $\mu$A from this device is transmitted through transistor 72 to the anode pins and transistor 52. In the event transistor 50 shorts, the source of transistor 72 is connected to the positive rail and a large current could otherwise flow through it. However, the gate of the transistor has a potential relative to the supply rail which is equal to the drop across transistor 40, which operates as a PN diode, and the gate-source voltage of transistor 42. The gate-source voltage of transistor 72, even if transistor 50 shorts, is thus limited to a value such that no more than 50 $\mu$A can flow through the output terminals of the device (the anode terminal being the case itself, and the cathode terminal being extended over a lead to the site to be stimulated). While 40 $\mu$A is higher than the desired current, it is still a safe current and the protection is achieved simply by providing the bipolar connections required for transistor 40.

Transistor 72 conducts all of the current delivered by transistor 50. The current delivered by transistor 50, nominally 20 $\mu$A, varies with the battery potential since transistor 50 mirrors the current through transistor 22, and this current is dependent primarily upon the battery potential once resistors R1 and R2 are selected. But for the output current of the device to vary only with the current through transistor 22, the current through transistor 50 should not be affected by its source-drain voltage drop. This drop can vary depending upon the impedance seen between the anode and cathode of the overall device, and the body impedance is neither predictable nor constant. Theoretically, transistor 50 operates in the saturated region so that its current depends only on the gate-source bias, and not on the drain-source voltage. However, it is only in theory that any curve on the $I_{DS}$-$V_{DS}$ characteristic of an FET device is flat, in the saturated region, for any given value of $V_{GS}$. In actual practice, the curve does slope due to the resistivity of the N bulk material of the chip. Moreover, the resistivity is process dependent. Because the output current would otherwise vary as $V_{DS}$ of transistor 50 varies even for a fixed $V_{GS}$, transistor 72 is provided in a "cascode" configuration. This transistor minimizes variations in the current through transistor 50 even as its drain-source voltage varies. Most of the voltage drop is across transistor 72 rather than transistor 50 so that the source-drain drop across transistor 50 is in the order of only a few hundred millivolts, essentially equal to the $\Delta$ applicable to the device. Transistor 72 functions to control transistor 50 to be a better constant-current source, whose current is dependent only upon its gate-source bias. Transistor 50 operates on the knee of its characteristic curve where there are the most significant changes in current for any change in $V_{DS}$.

Transistors 60, 70, 58, 56, 54 and 52 function as an "idle circuit". After the device is manufactured, it is usually stored for months until it is actually used. To maximize shelf life, it is desirable that minimum current be drawn from the battery. The idle circuit accomplishes this. It is only when the device is actually implanted, and the anode-cathode impedance is no longer an open circuit, that the currents described above actually start to flow in the circuit. In the bone growth stimulator described in the Wickham et al application, the quiescent current flow is about 1.7 μA even before implantation. In the device of our invention, however, the quiescent current drawn from the battery before implantation is only in the order of about 300 nA.

It was described above that 50 nA flows through transistor 54 due to its current mirror relationship with transistor 32. This is only true, however, when transistor 54 actually conducts; it does not conduct during normal operation. The gate-source voltage of transistor 52 is equal to the gate-source voltage of transistor 60 minus the drain-source drop across transistors 50 and 72. The latter is several hundred millivolts and the resulting gate-source voltage of transistors 52 is less than its threshold voltage. Consequently, when the device is implanted transistor 52 remains off. This, in turn, holds off transistor 58, by holding its gate low by transistor 54.

But in the event of an open circuit between the anode and cathode, i.e., before implantation and with no current flowing through transistor 50, the potential of the positive rail is applied to the gate of transistor 58 which thus conducts. The drain of this device which is normally held high in potential by transistor 70 now goes low, and since the drain of transistor 58 is connected to the gate of transistor 20, transistor 20 is held on. When transistor 20 conducts, it pulls up the gate of transistor 22. No current flows through transistor 22 and transistor 30 similarly remains off. Since transistor 30 provides the main current reference for the rest of the circuit, it is apparent that there is minimal current flow. It is only when anode-cathode current flows, and transistor 52 is held off, that transistor 58 is off to allow full powering of the device. This happens when the anode-cathode current causes the anode potential to drop below the supply voltage by at least 140 millivolts.

Before implantation, transistor 20 conducts, and current does flow through transistor 20 and resistors R1, R2 via transistor 23. As transistor 20 is fully on, devices 23 and 28 form a current mirror. There is a very small current flow through transistors 24, 26, 32 and other current mirrors. Approximately 300 nA flows in the overall circuit, the limited current being necessary to insure that transistor 58 remains on to hold transistor 20 on. The circuit is an "idle" circuit, not an "off" circuit, because some current does flow. The circuit idles so that when a load is applied across the anode and cathode, i.e., when the device is implanted, currents are already flowing in the circuit so that those devices which must turn on do so.

All of the circuitry to the left of transistor 72 previously described controls the delivery of current to the site to be stimulated (with a magnitude dependent on the potential of the battery) and it also limits current drain before implantation. The circuitry to the right of transistor 72 provides the monitoring function. The only connection of the two parts of the circuit to each other involves two current-mirror lines. The gate of transistor 46 is extended via conductor 34 to the right side of the circuit. This conductor is labeled "50 nA/P" because if it is connected to the gate of any P-channel device, whose source is connected to the positive rail, the potential on the line controls a current flow of 50 nA (per P), e.g., a 2P device will conduct 100 nA. Similarly, conductor 36, which is labelled "50 nA/N", if connected to the gate of any N-channel device whose source is connected to the negative rail, with control a current flow of 50 nA for an N device or 100 nA for a 2N device.

The key connection is that of line 34 to the gate of transistor 74. This transistor conducts a current whose magnitude is twice that of the current reference due to the various current mirror arrangements. Since the therapeutic current is also proportional to the current reference, the current through transistor 74 is necessarily proportional to the therapeutic current. Finally, the rate at which pulses are radiated by the monitoring circuit is directly proportional to the magnitude of the current through transistor 74, as will be described below, so that the rate at which the pulses are detected by an external monitor provides an accurate value of the therapeutic current.

The circuit is designed to transmit pulses at a relatively low rate. The maximum pre-set rate is 3.33 pulses per second, corresponding to the maximum pre-set therapeutic current of 20 μA. As the battery voltage falls from 3.0 volts to about 2.2 volts, the rate at which pulses are transmitted falls to approximately (2.2/3.0) (3.33) or about 2.44 pulses per second. Each time that a pulse is transmitted, there is a loss of energy, and to keep losses to a minimum a relatively low rate is used. Preferably, the lower limit for the rate is about one pulse per second because if the rate is still lower, then too much time is required for the external frequency counter (monitor) to actually provide a reading. (Basically, the frequency counter provides an indication of current value which is dependent upon the time between pulses, and it can take up two seconds to up-date the reading, for pulses which occur once each second. Also, the longer the up-date time, the greater the effect of noise-induced pick-up in the monitor.) In practice, there are losses due to the charging and discharging of stray capacitances. It is for this reason that an excessively high rate should not be used. Preferably, the upper limit for the rate is 20 pulses per second. The preferred rate range, at the start of device life, is 3.0–3.5 pulses per second.

As for each pulse itself, the important consideration is its fundamental frequency component. With too high a frequency component, eddy current losses in the titanium case are excessive. The fundamental frequency component of each pulse which is transmitted should be held below 20 kHz for this reason. On the other hand, if the fundamental frequency is too low, for example, below 1 kHz, the amount of energy required to excite the transmitting coil L1 may be too high for a battery-powered unit. In the illustrative of the invention, a 10-kHz fundamental frequency was selected. This requires a pulse width of 100 microseconds for each pulse which is transmitted. (In general, any pulse width between 50 and 500 microseconds may be employed, although a width of 100 microseconds is preferred.) A further advantage of 100-microsecond pulses is that the detection and amplification circuits in the monitor can be very straight-forward without requiring undue complexity in noise immunity and filtering circuits. The pulse width is constant at this value, and it is only the pulse repetition frequency which is varied in accordance with the therapeutic current magnitude.

Figure 5:
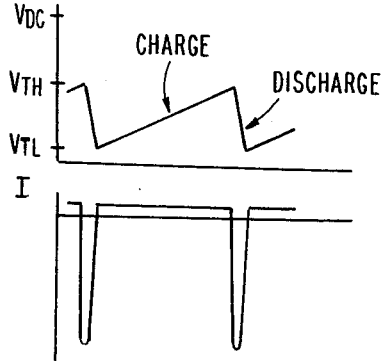
FIG. 5 depicts two waveforms which will be helpful in understanding the circuit operation.

The oscillator can be understood by first considering that capacitors C1 and C2 were charged, but are now in the process of discharging. The discharge of the capacitors is shown on the left side of the two waveforms in FIG. 5. As soon as the voltage across capacitors C1, C2 reaches a high threshold $V_{TH}$, as will be described below, the latch comprising gates 82, 84 is set. The output of gate 84 is switched high, so the output of inverter 88 is high. Transistor 80 conducts, and a large negative spike of current flows through the coil, as shown in the bottom waveform of FIG. 6. At the same time, the voltage at pins 13,14 decreases sharply, as shown in the upper waveform, due to the discharging of the capacitors.

While the capacitors are discharging, the high output of gate 88 drives transistor 98 on and holds transistor 92 off. Inverter 90 applies a low potential to the gate of transistor 102, so it is held on. Since transistors 94 and 96 comprise a current mirror, and transistor 96 conducts twice the current that transistor 94 conducts for the same gate-source bias, transistors 94 and 98 conduct only half the current of transistors 96 and 102. Were both of transistors 100 and 104 to conduct, because transistor 104 would have to conduct twice as much current, even though it is a smaller device, the Δ of transistor 100 would have to be much smaller than the Δ of transistor 104. Furthermore, at the start of the capacitor discharge, the source of transistor 100 is higher in potential than the source of transistor 104, since the latter is connected to the negative rail and the former is connected to pins 13,14 which are now high in potential. These conditions are sufficient to hold transistor 100 off; thus transistor 94 remains off. The high drain potential of transistor 94, which is connected to the gate of transistor 104, holds transistor 104 on. The drain of transistor 104 is thus low in potential to hold transistor 122 off. Consequently, the potential at the junction of the drain of transistor 122 and the drain of transistor 120, applied to the reset input 82-R of the latch, is high so that it has no effect on the latch.

As the voltage across the capacitors decreases as they discharge, the voltage at the source of transistor 100 decreases. Eventually, the voltage becomes low enough such that the transistor turns on. Current now flows through transistors 94, 98 and 100, and the drain of transistor 98 goes low to turn off transistor 104. The gate of transistor 122 now goes high so that this device turns on. When its drain potential goes low, the low potential at the 82-R reset input of the latch causes the latch to reset. This, in turn, causes transistor 80 to turn off, and the capacitors cease to discharge.

The 82-R input of the latch must now go high so that the latch can be set when the 84-S input goes low. The 82-R input does in fact go high again immediately. As soon as the latch resets and the output of inverter 88 goes low, transistor 92 turns on, and in turn causes transistor 104 to conduct so that the drain of transistor 122 goes high again. The net result is that only a very short reset pulse is generated when the capacitor voltage reaches the lower threshold value (shown in FIG. 6 as the $V_{TL}$ level. The reset circuit for the latch is designed to dissipate minimal current; transistors 98 and 100 are both on for only a very short interval while the reset pulse is generated after the capacitors discharge to the lower threshold, the lower threshold being approximately 100 millivolts. As the capacitors start to charge again, transistor 100 turns off for the reason described above. This readies the circuit to generate another reset pulse when the capacitors discharge to the lower threshold value.

Except during the short discharge pulse, transistor 78 is held on by the normally low potential at the output of inverter 88. Transistor 74 mirrors the current through transistor 46. Since its gate is connected to the 50 nA/P line and it is a 4P device, 200 nA flows through transistor 74—assuming that transistor 76 is on. This transistor is on only if pins 11,12 are grounded, and they are permanently grounded in the illustrative embodiment of the invention. Thus when transistor 78 is on, 200 nA flows through transistors 74, 76 and 78, and from the drain of transistor 78 to inductor L1, a 130-mH telephone coil. This constant current is used to charge the two capacitors through the coil, and it is shown in the second waveform of FIG. 5 between discharge current pulses. The time taken to charge the capacitors to the level $V_{TH}$ which controls a discharge pulse depends on the magnitude of the therapeutic current. The therapeutic current is derived from a current mirror which is dependent upon the current reference, and the same thing is true of the charging current through transistors 74, 76 and 78. Consequently, the time between discharge pulses is inversely proportional to the current reference and is a measure of the therapeutic current being delivered. It is the charging time which varies, not the discharge time; it always takes about 100 microseconds for the capacitors to discharge through the coil and to generate the current spike which results in the transmission of a pulse of radiant energy to the external monitor.

The circuitry to the right of the drawing, on FIG. 4, is the high threshold comparator for determining when the capacitor voltage reaches the high threshold—at which time the latch is set so that the capacitors can discharge once again. As mentioned above, in the illustrative embodiment of the invention, pins 11,12 are permanently grounded to enable the oscillator at all times. The low potential at the gate of transistor 140 holds this transistor off so that it can be ignored. But should external control of the oscillator be desired, a reed switch can be provided between pins 11,12 and ground. With the reed switch open, the drain of transistor 124 is high and causes transistor 140 to remain on. The low potential at the drain of transistor 140 holds transistor 144 off. The high potential extended through transistor 134 to the set input 84-S of the latch thus prevents setting of the latch even in the presence of noise, i.e., transistor 80 is held off. Although the low potential at the output of inverter 88 would ordinarily turn transistor 78 on, transistor 76 is held off by the high potential at the drain of transistor 124 so that no current flows through transistors 74, 76 and 78 to charge the capacitors. The same high potential at the drain of transistor 124 holds transistors 130 and 136 off so that no current flows through them and the connected transistors. Transistor 124 thus effectively disables the entire monitoring circuit to the right of transistor 72 so that there is minimum battery drain. It is only when the reed switch is operated and pins 11,12 are grounded (unless they are permanently grounded as they are in the illustrative embodiment of the invention) that a low potential appears at the gates of transistors 76, 130 and 136 to turn on these devices so as to enable both the charging current source for the capacitor and the high threshold comparator. Similarly, the low potential at the gate of transistor 140 holds this transistor off so that the latch is not held in the set state.

The provision of a reed switch control means that during most of the implanted life of the stimulator, there need not be a constant drain from the battery of approximately 0.8 μA, the current required to drive the oscillator. The oscillator would be enabled only when a magnet is applied in the vicinity of the reed, as is standard practice in the heart pacer art. This would result in an extension of the battery life by approximately 5%. In the illustrative embodiment of the invention, however, a reed switch is not employed because the decrease in battery life due to the particular oscillator employed is so minor that it is preferable to have the oscillator run continuously rather than to employ a reed switch which would necessarily have the lowest reliability of any component in the overall system.

The high threshold voltage of about 1.5 volts appears at the gate of transistor 142. Transistor 136 is held on by the ground potential at its gate. Transistor 132 conducts 100 nA since its source is connected to the positive rail and its gate is connected to the 50 nA/P line 34. This current flows through transistors 146 and 148. Because the two gates are connected to each other, the overall voltage across the two devices is the sum of the threshold voltage of a P-channel device and the threshold voltage of an N-channel device (both of which change with age, but in opposite directions). The reference voltage is thus equal to the sum of the N and P thresholds, and is relatively independent of the supply voltage. Whatever the threshold, during manufacture capacitors C1 and C2 are adjusted to provide the desired pulse repetition frequency. Capacitor C1 is a low leakage ceramic capacitor of 47 nF. Capacitor C2 is similarly a low leakage ceramic component, but its value is selected to provide a 3.33 Hz repetition rate for a 20 μA current delivered between the anode and cathode during the production test.

The gate of transistor 150 is connected to the 50 nA/N line 36, and since transistor 150 is a 2N device, 100 nA flows through it. This current is divided between transistors 126 and 142. During the discharge of capacitors C1 and C2, and after the capacitors start to charge, the potential at pins 13,14 is low and the gate of transistor 126 is at a voltage less than the potential applied to the gate of transistor 142. The 100 nA bias current through transistor 150 flows through transistors 138 and 142, rather than through transistors 128 and 126. But as the capacitor voltage increases, a point is reached at which transistors 126 and 142 share the bias current. As the voltage at the gate of transistor 126 increases still further, transistor 126 turns on harder, and reduces the potential at the gate of each of transistors 128 and 138. This causes the drain of transistor 138 to increase in potential, thus turning on transistor 144. The low potential at the drain of transistor 144 sets the latch so that the capacitors can now discharge. As soon as the capacitor voltage drops during the discharge, transistor 126 turns off and transistor 142 conducts the full bias current once again.

Any standard frequency counter can be used for the monitor itself. Basically, the monitor provides an output whose value is dependent upon the pulse repetition rate. It should be noted that the larger the current, the shorter the time required for the capacitors to charge to the high threshold level, i.e., the higher the repetition rate. If the monitor functions to detect the time interval between pulses, a shorter time interval corresponds to a higher therapeutic current. To provide a convenient read-out for the physician, the monitor should directly convert the time interval in a reciprocal manner to provide an indication of the current.

The monitor itself can be straight-forward in design. Preferably, a Delyanis filter centered at 10 kHz and with a 3 dB passband of ±400 Hz is employed in the input detector. Each pulse (at the nominal rate of 3.33 per second) resets a counter which is then driven by a 1-kHz oscillator. The count in the counter is latched upon the receipt of each pulse, so that while the counter is counting between any two pulses, the previous value is available for processing. Another counter is driven by a still higher frequency, e.g., 1 MHz. This counter is a "programmable-divide-by-N" device which generates an output pulse each time that it counts to the last latched value. It is thus apparent that the greater the latched value, corresponding to a longer time interval between pulses, the lower the frequency of the output pulses from the high frequency counter. It is the frequency of the latter counter which is actually displayed in terms of a current value, because the longer the time between pulses, the lower the therapeutic current. The monitor is set to provide a reading of 20 μA for a detected pulse rate of 3.33 Hz.

It is to be understood that this arrangement is only illustrative of a suitable monitor design; all that is required is that the monitor convert the time interval between successive pulses into a value which represents current, longer time intervals corresponding to lower values of current. The use of counters in the manner described is a convenient way to achieve the reciprocal relationship between time intervals and currents. Also, the coil used in the receiver for detecting the pulses radiated from the stimulator should preferably be enclosed in a five-sided mumetal shield; this will prevent the coil from being excited by any radiation other than that at the open end of the shield which is placed in the monitor so that it can be positioned as close as possible to the radiating coil in the stimulator.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What we claim is:

1. A monitorable implantable bone growth stimulator comprising an hermetically-sealed metal container and at least one electrode lead exiting therefrom; said container having therein a power source, circuit means powered by said power source for delivering a constant direct current over said electrode lead to a bone to be stimulated, a transmit-only coil, and means for generating current pulses through said coil at a rate dependent upon the magnitude of said constant direct current for radiating a monitorable signal externally of said container, said circuit means including a current reference and means for delivering a current which is proportional to and dependent upon said current reference, said current pulse generating means operating at a rate which is likewise proportional to and dependent upon said current reference.

2. A monitorable implantable bone growth stimulator in accordance with claim 1 wherein changes in said current reference are primarily dependent on changes in the magnitude of said power source.

3. A monitorable implantable bone growth stimulator in accordance with claim 1 wherein said current pulse generating means operates continuously after implantation.

4. A monitorable implantable bone growth stimulator in accordance with claim 3 wherein said current pulse generating means generates pulses at a rate in the range 1–20 pulses per second.

5. A monitorable implantable bone growth stimulator in accordance with claim 4 wherein the pulse rate is no higher than 3.5 pulses per second.

6. A monitorable implantable bone growth stimulator in accordance with claim 3 wherein said current pulse generating means generates pulses having a duration in the range 50-500 microseconds.

7. A monitorable implantable bone growth stimulator in accordance with claim 1 wherein said current pulse generating means generates pulses at a rate in the range 1-20 pulses per second.

8. A monitorable implantable bone growth stimulator in accordance with claim 2 wherein the pulse rate is no higher than 3.5 pulses per second.

9. A monitorable implantable bone growth stimulator in accordance with claim 1 wherein said current pulse generating means generates pulses having a duration in the range 50-500 microseconds.

10. A monitorable implantable bone growth stimulator in accordance with claim 1 further including means for selectively disabling operation of said current pulse generating means.

11. A monitorable implantable bone growth stimulator in accordance with claim 1 further including automatic means responsive to the absence of current in said electrode lead for causing said circuit means to idle whereby battery life is extended.

12. A monitorable implantable bone growth stimulator in accordance with claim 11 further including means for inhibiting operation of said current pulse generating means when said circuit means is idling.

13. A monitorable implantable bone growth stimulator in accordance with claim 1 wherein said current pulse generating means includes a charge/discharge circuit responsive to high and low threshold voltages, and said high threshold voltage is derived from a pair of P-channel and N-channel transistors having their gates connected together.

14. A monitorable implantable bone growth stimulator comprising a container and at least one electrode lead exiting therefrom; said container having therein a non-rechargeable power source, circuit means powered by said power source for delivering a constant current over said electrode lead to a bone to be stimulated, and means for generating pulses at a variable rate dependent upon the magnitude of said delivered current to radiate a monitorable signal externally of said container, said circuit means including a current reference and means for delivering a current which is proportional to and dependent upon said current reference, said current pulse generating means operating at a rate which is likewise proportional to and dependent upon said current reference.

15. A monitorable implantable bone growth stimulator in accordance with claim 14 wherein changes in said current reference are primarily dependent on changes in the magnitude of said power source.

16. A monitorable implantable bone growth stimulator in accordance with claim 14 wherein said current pulse generating means operates continuously after implantation.

17. A monitorable implantable bone growth stimulator in accordance with claim 16 wherein said current pulse generating means generates pulses at a rate in the range 1-20 pulses per second.

18. A monitorable implantable bone growth stimulator in accordance with claim 17 wherein the pulse rate is no higher than 3.5 pulses per second.

19. A monitorable implantable bone growth stimulator in accordance with claim 16 wherein said current pulse generating means generates pulses having a duration in the range 50-500 microseconds.

20. A monitorable implantable bone growth stimulator in accordance with claim 14 further including means for selectively disabling operation of said current pulse generating means.

21. A monitorable implantable bone growth stimulator in accordance with claim 14 further including automatic means responsive to the absence of current in said electrode lead for causing said circuit means to idle whereby battery life is extended.

22. A monitorable implantable bone growth stimulator in accordance with claim 21 further including means for inhibiting operation of said current pulse generating means when said circuit means is idling.

23. A monitorable implantable bone growth stimulator in accordance with claim 14 wherein said current pulse generating means includes a charge/discharge circuit responsive to high and low threshold voltages, and said high threshold voltage is derived from a pair of P-channel and N-channel transistors having their gates connected together.

* * * * *